United States Patent [19]

Street

[11] Patent Number: 5,351,408
[45] Date of Patent: Oct. 4, 1994

[54] CERVICAL MEASUREMENT APPARATUS

[76] Inventor: Robert E. Street, 848 W. Michigan Ave., Marshall, Mich. 49068

[21] Appl. No.: 33,407

[22] Filed: Mar. 19, 1993

[51] Int. Cl.$^5$ .......................... A61B 5/103; G01B 5/20
[52] U.S. Cl. ................................. 33/512; 33/514.2; 33/561.3; 128/774
[58] Field of Search .............. 33/512, 511, 514.2, 33/515, 561.3; 128/774

[56] References Cited

U.S. PATENT DOCUMENTS

| | | | |
|---|---|---|---|
| 2,378,039 | 6/1945 | Schenker | 33/514.2 |
| 4,756,090 | 7/1988 | Pedrow | 33/512 |
| 4,903,412 | 2/1990 | Pedrow | 33/512 |
| 4,993,164 | 2/1991 | Jacobsen | 33/512 X |
| 5,101,835 | 4/1992 | DelRe | 33/512 |

*Primary Examiner*—Christopher W. Fulton
*Attorney, Agent, or Firm*—Flynn, Thiel, Boutell & Tanis

[57] ABSTRACT

Measurement apparatus for determining parameters of a patient's neck comprises a table for positioning the patient's torso during measurement, a head positioning mechanism disposed on the table for positioning the patient's head during measurement, and a measuring mechanism for moving a cervical pad in a first direction corresponding to the length of the patient's neck between the torso and the head and in a second direction transverse to the first direction toward the concavity of the patient's neck. The measuring mechanism includes a base that is movably mounted on the table for movement relative thereto in the first direction, a cervical pad movably mounted on the base for movement relative thereto in the second direction and having an arcuate profile selected in dependence on the curvature of the patient's neck, and moving device for moving the cervical pad in the second direction to engage the cervical region of the patient when the patient's torso and head are positioned for measurement. The distances that the base and cervical pad are moved in the respective first and second directions to engage the cervical pad with the cervical region of the patient and the selected profile of the cervical pad means provide parameters for the manufacture of a cervical pad for use by the patient.

22 Claims, 9 Drawing Sheets

CERVICAL MEASUREMENT APPARATUS

FIELD OF THE INVENTION

The present invention relates to a cervical measurement apparatus useful for obtaining from a patient cervical parameters that can be employed in the manufacture of custom-fit orthopedic cervical pillows for individual patients.

BACKGROUND OF THE INVENTION

Patients having a cervical kyphosis disorder, such as typically abnormal curvature of the cervical vertebrae, often are advised to use a cervical traction device to restore the cervical curvature to a more normal profile. In this event, the patient may be able to purchase a mass produced cervical pillow or instructed in rolling a towel for use to this end. Unfortunately, given the wide variety of patient physiques (i.e. cervical curvatures, neck sizes, head sizes, shoulder sizes and the like) that are encountered in patients, a mass produced cervical pillow or a rolled towel will seldom provide a truly custom fit for the individual patient.

As a result, the patient is oftentimes advised to simply roll a towel into a cylindrical form of suitable size to use during prescribed cervical traction treatments in lieu of a mass produced cervical pillow or rolled towel.

Similarly, many patients have a need for a cervical pillow for use during sleeping and resting periods when the patient is lying on his or her side. The cervical pillow should conform well to the patient's neck to provide adequate support. However, given the wide variety of patient physiques that are encountered, a mass produced pillow or a rolled towel will seldom provide a truly custom fit for the individual patient.

There is a need to provide a cervical measurement apparatus that would allow the fabrication of cervical pillows to configurations and sizes custom-fit to the individual patient for use during traction treatment of the cervical curvature disorder, or during sleeping and resting periods to support the patient's neck properly.

U.S. Pat. Nos. 4 756 090 and 4 903 412 describe a sizing kit for determining an appropriate size for an orthopedic pillow for use by a patient. The sizing kit comprises a series of differently sized and curved sizing members that can be stacked one atop the other to conform the patient's cervical profile and size and also to facilitate storage. This sizing kit is disadvantageous in that a plurality of sizing members must be handled and stored.

An object of the present invention is to provide an improved cervical measurement apparatus that will allow fabrication of a cervical pillow to configurations and sizes in accordance with measured parameters obtained from the individual patient so to enable the manufacture of a cervical pillow custom-fit to that patient.

SUMMARY OF THE INVENTION

The present invention provides a measurement apparatus for determining parameters of a patient's neck that will allow the fabrication of a cervical pillow to configurations and sizes in accordance with the measured parameters so to enable the manufacture of a cervical pillow custom-fit to that patient. One embodiment of the measuring apparatus of the invention comprises table means for positioning the patient's torso during measurement, head positioning means for positioning the patient's head during measurement, and measuring means for moving a cervical measuring pad means in a first direction corresponding to the length of the patient's neck between the torso and the head and in a second direction transverse to the first direction toward the concavity of the patient's neck. The measuring means includes base means movable in the first direction, cervical measuring pad means movably mounted on the base means for movement relative thereto in the second direction and having an arcuate profile selected in dependence on the curvature of the patient's neck, and means for moving the cervical measuring pad means in the second direction to engage the cervical region of the patient when the patient's torso and head are positioned for measurement.

The distances that the base means and the cervical measuring pad means are moved in the respective first and second directions to engage the cervical pad means with the cervical region of the patient and the selected profile of the cervical pad means provide parameters for the manufacture of a cervical pillow custom-fit to the patient.

In a one particular embodiment of the invention, the head positioning means comprises base means movable in the first direction, head pad means movably mounted on the base means for movement in a direction parallel to said second direction, and means for moving the head pad means to engage and support the head of the patient during measurement.

In another particular embodiment of the invention, a base member for the measuring means and the head positioning means includes a plurality of reference position indicators spaced along the first direction proximate the base means of the measuring means. Each indicator provides a respective reference measurement start position for the base means in dependence on the particular cervical measuring pad means profile selected. The base member includes distance scale means proximate the indicators for determining the distance that the base means of the measuring means is moved relative to a respective reference position. The measuring means includes distance scale means for determining the distance that the cervical measuring pad means is moved in the second direction to engage with the patient's neck.

In still another embodiment of the invention, the cervical measuring pad means can comprise relatively movable sections that permit variations in the curvature of the pad profile as well as in the length thereof so as to provide further parameters that also can be used in the manufacture of a cervical pillow.

The present invention also provides a measuring apparatus for determining parameters of a patient's neck that will allow the fabrication of a cervical traction pillow to configurations and sizes in accordance with the measured parameters so to enable the manufacture of a cervical traction pillow custom-fit to that patient. The apparatus comprises means for positioning the back of the patient's torso and back of the head in a downwardly facing position during measurement, and measuring means for moving a cervical traction pad means in a first direction corresponding to the length of the patient's neck between the torso and the head and in a second direction transverse to the first direction toward the concavity of the patient's neck. The measuring means includes base means movable in the first direction, cervical traction pad means movably mounted on the base means for movement relative thereto in the second direction, and means for moving the cervical traction pad means in the second direction to engage the cervical region of the patient when the patient's torso and head are positioned for measurement.

The cervical traction pad means includes an arcuate profile selected in dependence on the curvature of the patient's neck. The profile includes a longitudinal groove to accommodate the patient's spinal vertebrae.

The distances that the base means and cervical traction pad means are moved in the respective first and second directions to engage the cervical pad means with the cervical region of the patient and the selected profile of the cervical pad means provide parameters for the manufacture of a cervical traction pillow for use by the patient.

The cervical traction pad means can comprise relatively movable sections that permit variations on the curvature of the pad profile as well as length thereof so as to provide further parameters that also can be used in the manufacture of a cervical traction pillow or pad.

These and other features of the invention will become apparent in more detail form the following detailed description taken with the drawings.

BRIEF DESCRIPTION OF THE DRAWINGS

FIGS. 8A, 8B are respective front and side elevational views of the head pad assembly.

DETAILED DESCRIPTION

Figure 1:
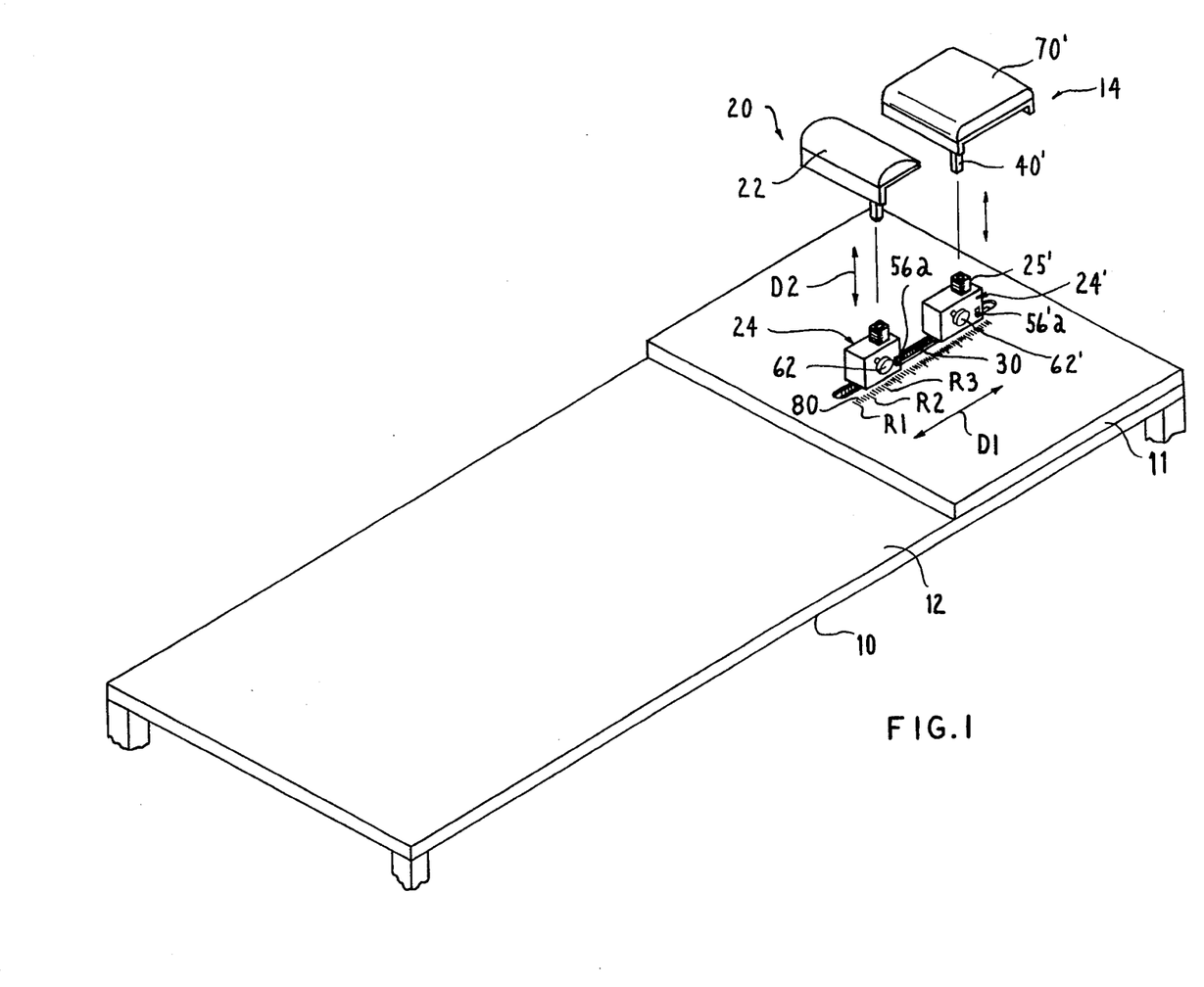
FIG. 1 is a perspective view of a cervical measuring apparatus in accordance with one embodiment of the invention.
Figure 2:
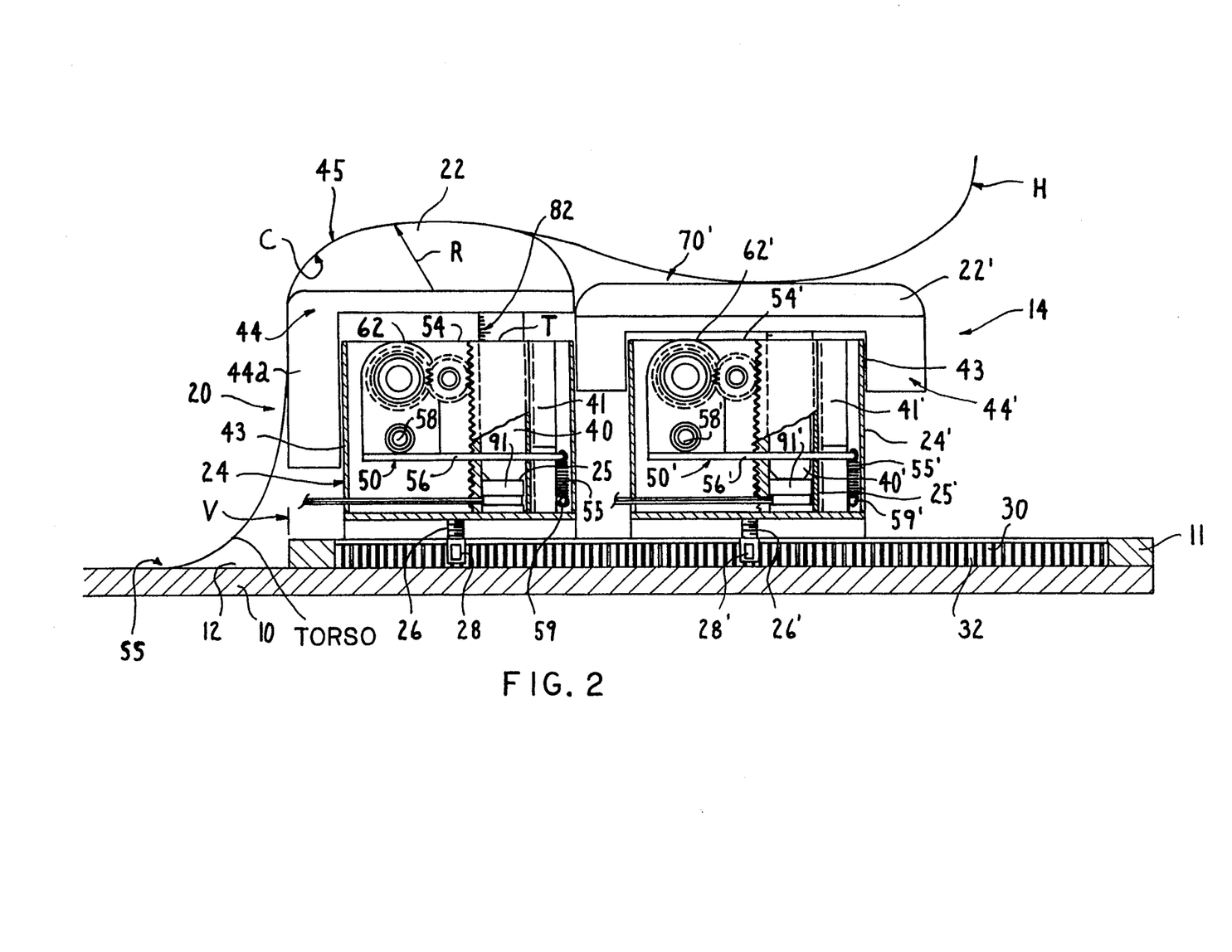
FIG. 2 is a sectional view of a torso positioning table, measuring mechanism and head positioning mechanism in accordance with one embodiment of the invention with a patient's torso and head partially illustrated.

Referring to FIGS. 1–2, a measurement apparatus of the invention for determining parameters of a patient's neck is illustrated. The measurement apparatus permits fabrication of a cervical pillow to configurations and sizes in accordance with the measured parameters so to enable the manufacture of a cervical pillow custom-fit to that patient.

The measurement apparatus comprises a table 10 having a horizontal upper surface 12 for properly positioning the patient's torso during measurement; e.g. the side SS of the patient's torso as shown best in FIG. 2. The apparatus also includes a head positioning means 14 and measuring means 20 disposed on a secondary table base member 11. The base member 11 preferably is disposed atop the table 10 for properly positioning the patient's head during measurement; e.g. the side of the patient's head H as shown best in FIG. 2. Typically, the base member 11 is simply set on the table 10 temporarily to take measurements. Alternately, the base member 11 can be formed integrally with the table 10. However, a removable base member 11 is advantageous to allow the table 10 to be put to other uses when cervical measurements are not being taken. A pad (not shown) can be positioned on the table surface 12 to provide an upper torso supporting surface generally coplanar with the upper surface of base member 11.

The parameters used in the fabrication of the cervical pillow are obtained from the patient by the measuring means 20 disposed on secondary table base member 11 between the upper table surface 12 and the head positioning device 14. To this end, the measuring means 20 is constructed in a manner that permits a cervical measuring pad 22 to be moved in a first direction D1 corresponding to the length of the patient's neck between the torso and the head and in a second direction D2 transverse to the first direction toward the concavity C of the patient's neck (i.e. in a vertical direction in FIGS. 1–2).

Figure 3:
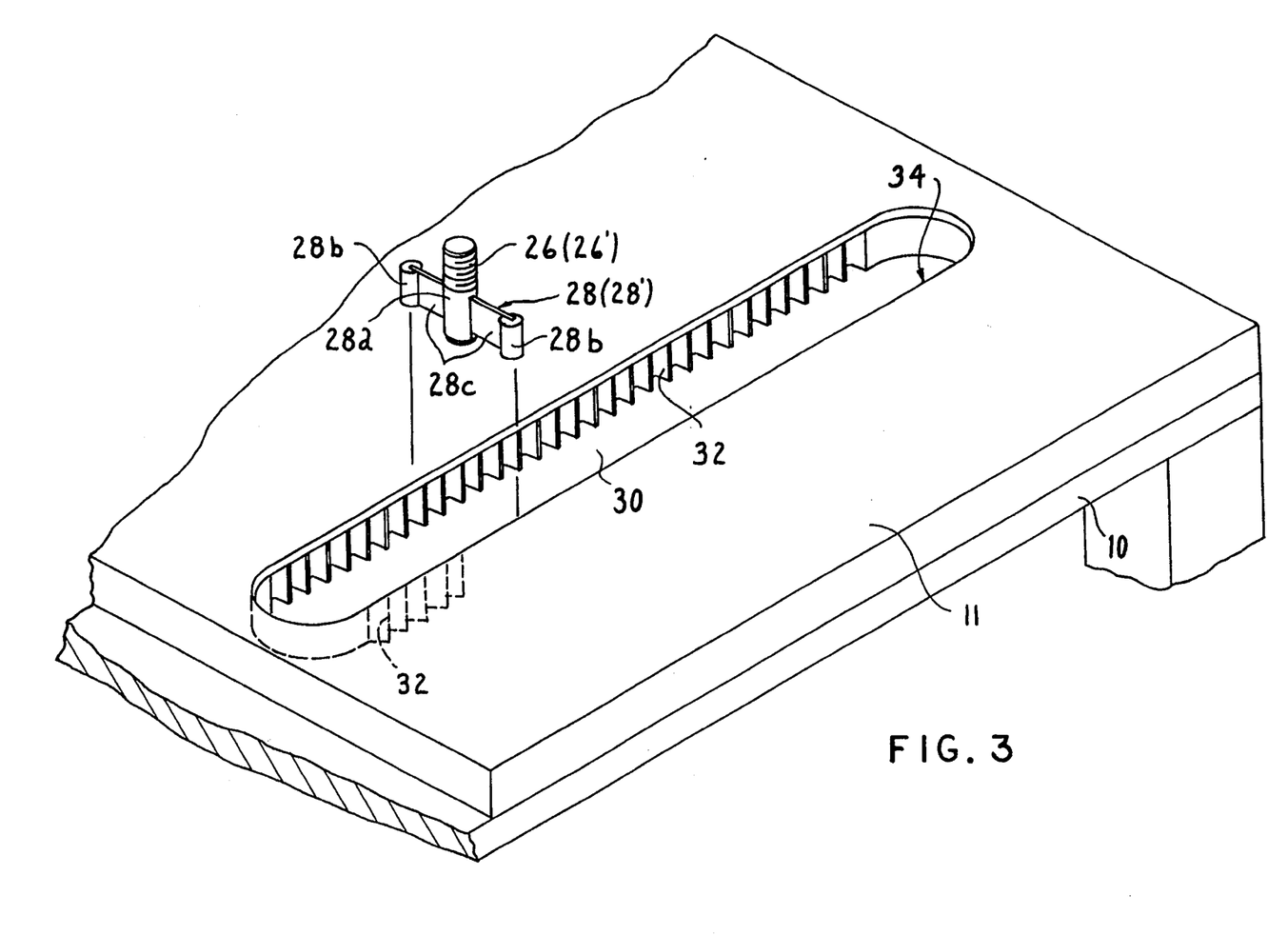
FIG. 3 is an enlarged perspective view of a base member having a groove and ratchet teeth for cooperation with the measuring mechanism and head positioning mechanism.

The measuring means 20 includes a base 24 in the form of an enclosure or box 43 movably mounted on the base member 11 for movement relative thereto in the first direction D1 and cervical measuring pad 22 movably mounted on the base 24 for movement relative thereto in the second direction D2. The enclosure 43 has a threaded shaft 26 extending downwardly from the bottom wall thereof into a groove 30 formed in the base member 11. The shaft 26 includes a laterally extending, ratchet-engaging cross member 28 having a hub 28a threaded thereon and having opposite ends 28b that engage the ratchet teeth 32 formed on undercut shoulders 34 formed on opposite sides of the groove 30 in the base member 11 as shown in FIGS. 1–2. The cross member 28 includes relatively thin, flexible web portions 28c between the hub 28a and the ends 28b, FIG. 3, to permit ratchet-type movement of the cross member 28 relative to the ratchet teeth 32 in order to adjust the position of the measuring means 20 in the direction D1 as will be explained.

The measuring pad 22 is disposed on a support post 40 that is received in an upstanding tubular member 25 of the base enclosure 24 for vertical movement relative to the base 24 in the vertical direction D2. The cervical measuring pad 22 includes a lower, metal, plastic or wood platform or base platform 44 to which the post 40 is connected. The pad 22 is mounted on the platform 44 and is configured to have a flat front elevational upper surface profile 43, FIG. 6, and an arcuate side elevational upper surface profile 45, FIGS. 2 and 5, at least a portion of which is defined by radius R that, as will be explained, is selected by the operator of the apparatus in dependence on the curvature of the patient's neck; i.e. to match the curvature of the patient's neck.

Figure 9A:
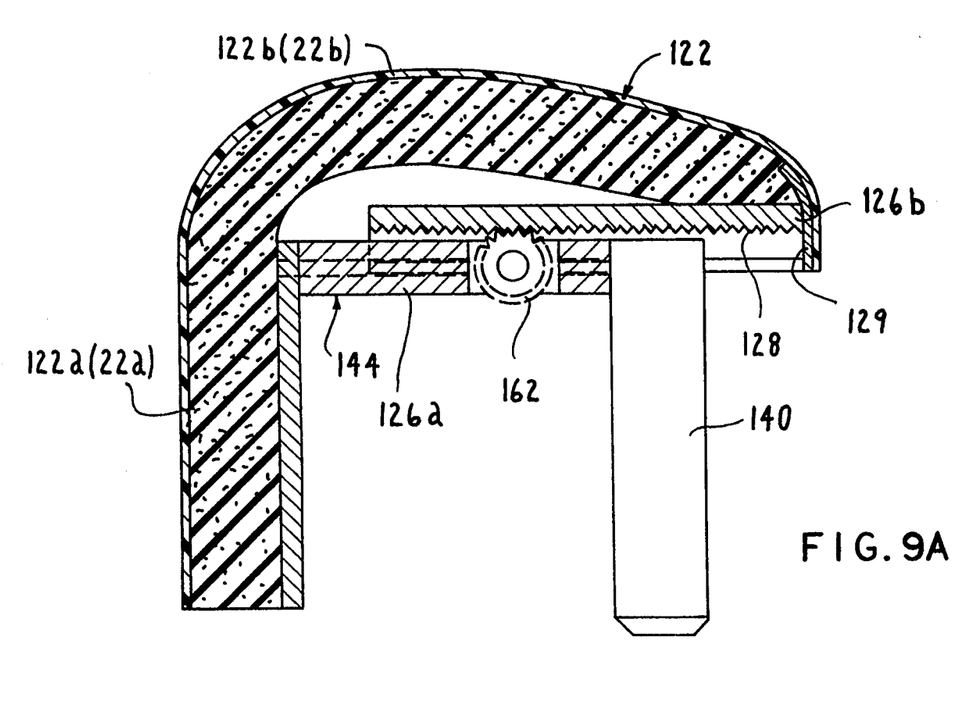
FIG. 9A is a sectioned side view of another cervical pad assembly that allows movement of first and second pad sections relative to one another.

The pad 22 may comprise a molded plastic foam core 22a covered by a plastic outer sheet or shell 22b as shown, for example, in FIG. 9A for another pad embodiment of the invention. Other types of pad constructions can be used, however, in the invention.

The lower platform 44 includes a depending flange 44a overlapping the base 24 on the side thereof facing the patient's torso T. The flange 44a provides a vertical reference plane V relative to which the patient's lower shoulder in FIG. 2 is positioned prior to measurement taking. As is apparent in FIG. 2, the vertical plane V includes the vertical end of base member 11.

Figure 4A:
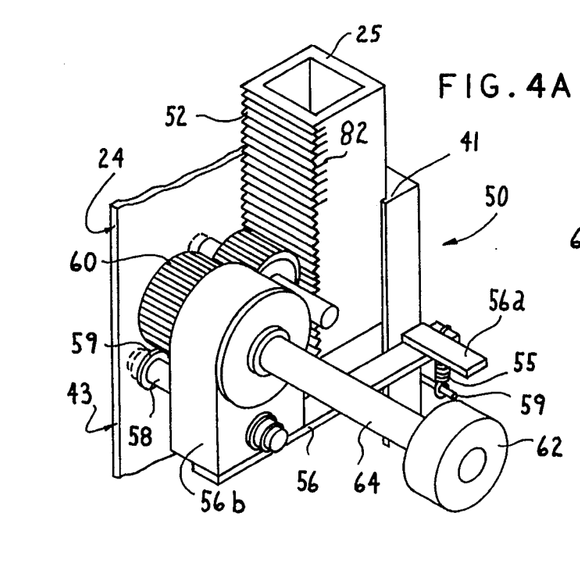
FIGS. 4A, 4B are perspective views of a cervical pad elevation mechanism useful in one embodiment of the invention with the mechanism shown in different operative positions.
Figure 4B:
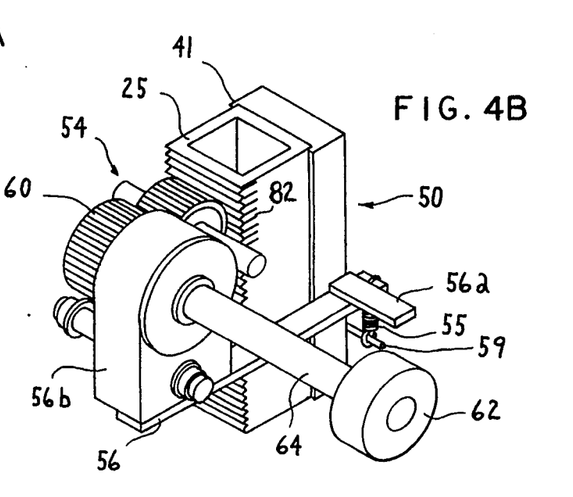

A manually actuated pad moving means 50 is provided on base 24 for moving the cervical measuring pad 22 in the second direction D2 to engage the cervical region of the patient when the patient's torso T and head H are positioned for measurement as shown in FIG. 2. In particular, referring to FIGS. 2, 4A, 4B, the pad post 40 is received in the upstanding tubular member 25 which is movably mounted on a guide 41 formed in the base enclosure 43 having four upstanding walls, top wall and bottom wall as shown in FIG. 1-2. The tubular member 25 includes a toothed rack 52 that is driven up or down by a gear train 54 mounted in the base enclosure 43. In particular, the gear train 54 is mounted on opposite enclosure side walls (one shown in FIG. 4A) by an axle or pin 58 and bushing 59 between the side walls so that the gear train can be pivoted about the axis of the axle 58.

The gear train 54 can be manually pivoted about the axle by pivoting of a support plate 56 on which the gear train 54 is carried. In particular, the support plate 56 includes a finger tab 56a that is exposed through a suitable opening in the adjacent sidewall of the enclosure 43, FIG. 1. When the finger tab 56a is raised, the gear train 54 will be pivoted counterclockwise about the axle 58 away from the rack 52 to effect disengagement therefrom for purposes to be described. The gear train 54 is pivoted against the bias of spring 55 that normally biases the gear train 54 in meshing engagement with the toothed rack 52. The lower end of the spring 55 is held fixed to the enclosure 43 by a cross pin 59 extending between the enclosure sidewalls.

The gear train 54 is pivotally mounted on the enclosure 43 such that the gear train can be readily disengaged from the toothed rack 52 during use of the measurement apparatus to rapidly lower/raise the cervical measuring pad 22 relative to the patient's neck. For example, after the desired neck parameters have been taken, the gear train 54 can be released from engagement with toothed rack 52 by appropriately pivoting finger tab 56a so that the pad 22 can be rapidly lowered away from the patient's neck.

The gear train 54 is driven by a pinion 60 connected to a manually rotatable knob 62 via a shaft 64. The shaft 64 is rotatably mounted by anti-friction bushing or bearings (not shown) in a housing 56b on the support plate 56 such that rotation of the knob 62 will cause the pinion 60 to rotate and drive the gear train 54 in one direction or the other depending on the direction of knob rotation.

The head positioning means 14 is constructed to permit the head pad 70' to be moved in the horizontal direction D1 and a vertical direction parallel with the direction D2 so as to be adjustable to properly support the patient's head during measurement. To this end, the head positioning means 14 includes operative components like those employed for the measuring means 20 to achieve such horizontal and vertical adjustability. In FIGS. 1, 2, and 4A-C, such like components of the head positioning means are designated with like reference numerals primed.

Figure 5:
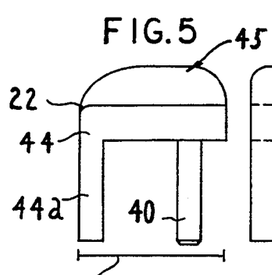
FIG. 5 is a side elevational view of the cervical pad assembly.
Figure 6:
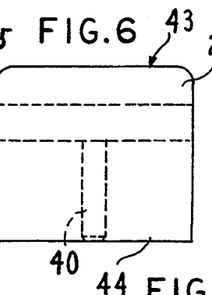
FIG. 6 is a front elevational view of the cervical pad assembly.
Figure 8A:
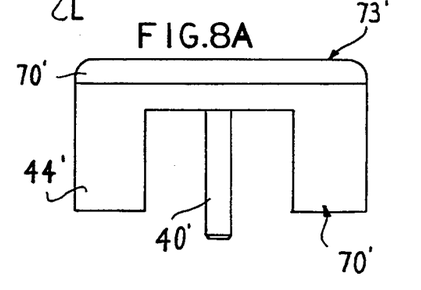

The head positioning means 14 differs from the measuring means 20 in having head pad 70' with flat, horizontal upper surface profiles 73', 75' in both the side and front elevations, FIGS. 8A and 8B, rather than the arcuate side elevational profile 45 of the cervical measuring pad 22 in the side elevation, FIGS. 2 and 5. The head pad 70', however, is otherwise constructed like the cervical measuring a pad 22; i.e. having a resilient plastic foam core and outer, plastic sheet or shell.

In use of the apparatus, the patient is positioned on the table 10 with the side SS of the body torso resting on the table top surface 12 as shown partially in FIG. 2 with the patient's shoulder abutted against the flange 44a of the cervical measuring pad 22. The head positioning means 14 is adjusted horizontally in the direction D1 to position the head pad 70' beneath the patient's head H as shown in FIG. 2. Then, the knob 62' is rotated by the operator of the measurement apparatus to raise the head pad 70' in the vertical direction parallel to direction D2 to engage and support the patient's head as also shown in FIG. 2.

Figure 7A:
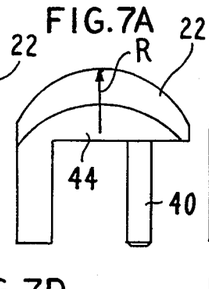
FIG. 7A–7G are side elevational views of other cervical pad assemblies useful with the apparatus of FIG. 1.
Figure 7B:
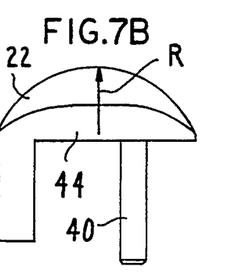
Figure 7C:
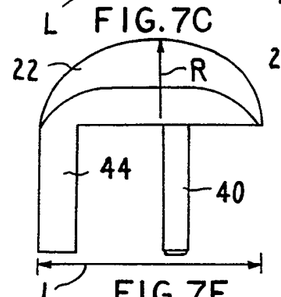
Figure 7D:
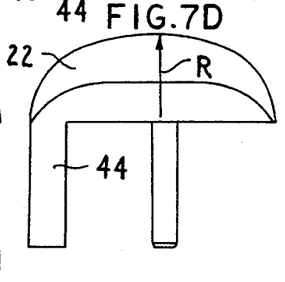
Figure 7E:
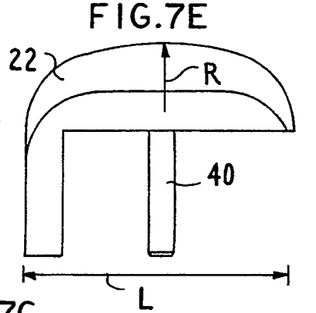
Figure 7F:
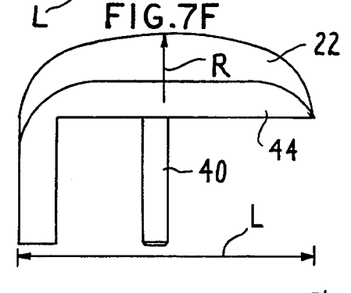
Figure 7G:
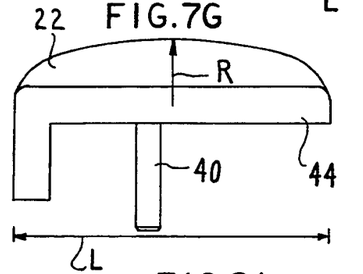

The measuring means 20 is initially located at one of a plurality of reference position indicators R1, R2, R3, etc. marked on the base member 11, FIG. 1, in dependence on the particular cervical measuring pad 22 chosen by the operator. That is, the measuring means 20 is located at reference position R2 if a different pad is used, and so on. For example, the cervical measuring pad 22 shown in FIGS. 1-2 and 5-6 can be replaced by a differently configured/sized measuring pad to initially accommodate the perceived different neck curvature/size of a particular patient. The invention thus envisions in one embodiment an inventory of different cervical measuring pads for use with the measurement apparatus. A typical inventory of cervical measuring pads for use with the apparatus can include pads of the type illustrated in FIGS. 7A through 7G that can be interchanged with one another on the base 24 to accommodate different patient neck curvatures/sizes to be encountered. The cervical measuring pads will have different radiused portions (e.g. radius or radii R) and lengths L as is apparent from FIGS. 7A through 7B.

The reference position indicator R1 typically will be located at a longitudinal position corresponding to the vertical plane V. A particular cervical measuring pad, such as pad 22, will be used in connection with the taking of measurements relative to reference position R1. A different cervical measuring pad will be used in connection with the taking of measurements relative to reference position indicator R2. A still different cervical measuring pad will be used in connection with the taking of measurements relative to reference position indicator R3 and so on for each reference position marked on the table base member 11. The reference positions R1, R2, etc. correspond to particular ratchet teeth 32 on the base member 11 so that the base 24 of the measuring means 20 is retained initially thereat. Use of cervical measuring pads for particular reference positions allows a time for effective initial, rough adjustment of the cervical measuring pad to accommodate different neck curvatures/sizes and will result in overall time savings in conducting the necessary measurements.

To conduct the cervical measurement, the patient is properly positioned on the table 10 and the head positioning means 14, the latter being adjusted horizontally in direction D1 and vertically in a direction parallel to direction D2 to support the head H as shown in FIG. 2. The base 24 of the measuring means 20 initially located at the particular reference position indicator R1, R2, R3 or the like in dependence on the particular cervical measuring pad 22 chosen by the operator.

The base 24 then is moved manually (providing ratchet action between cross member 28 and teeth 32) from the particular reference position in the longitudinal direction D1 to provide a best fit to the length of the patient's neck. This movement corresponds to a distance that is determined from a linear distance scale 80 disposed proximate the groove 30 as shown in FIG. 1. This distance comprises one parameter to be used in fabrication of the cervical pillow for the patient. As a result, the distance of movement of the base 24 is recorded by the operator of the apparatus.

Then, the cervical measuring pad 22 is raised by rotation of knob 62 until the pad 22 is snugly fit to the patient's neck curvature. The vertical distance that the pad 22 is raised is determined from the linear distance scale 82 on the post 40 and tubular member 25 using the top surface T of the base 24 as the reference line for sighting. The distance of vertical pad movement is recorded and is another parameter used to fabricate the cervical pillow or pad for the patient.

The distances that the base 24 and the cervical measuring pad 22 are moved in the respective first and second directions D1, D2 to engage the cervical measuring pad 22 with the cervical region of the patient as well as the selected profile of the cervical measuring pad 22 selected for the measurement (i.e. radius R and length L) provide parameters that are recorded and used in the manufacture of a cervical pillow custom-fit to the patient.

Figure 4C:
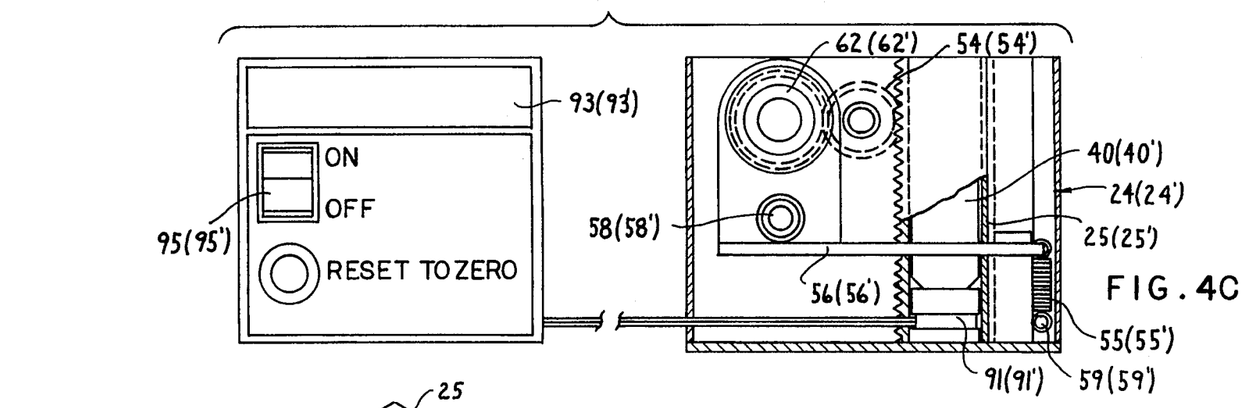
FIG. 4C is a side view of the elevation mechanism of FIGS. 4A, 4B and a weight scale control unit therefor.

In FIG. 2, the bottoms of the tubular member 25, 25' of the respective measuring means 20 and head positioning means 14 are shown closed off by an optional weight measuring device 91, 91' such as an electronic weight scale fixed to the tube bottoms. Each weight scale 91, 91' is connected electrically to a read out 93, 93' and on/off switch 95, 95' as shown in FIG. 4C. Using the weight scales read outs, the operator of the measurement apparatus can attempt to balance the weight of the patient's neck and head regions evenly between the measuring means 20 and head positioning means 14 during the measurement of the parameters for pillow fabrication.

In lieu of using the aforementioned inventory of cervical measuring pads 22 shown in FIGS. 5–7G, the cervical measuring pad 122 shown in FIG. 9A may be used with the measurement apparatus of FIGS. 1–2. The cervical measuring pad 122 is disposed on a platform 144 having relatively movable platform sections 126a, 126b. The lower section 126a includes a tubular post 140 that is received in the tubular member 25 of the base enclosure 43 of the measuring means 20 for vertical movement in direction D2 by the pad moving means described above. The upper section 126b is movably mounted on the lower section 126a and includes a toothed rack portion 128. A rotatable knob 162 is mounted on the lower platform 126a and is connected to a pinion 160 that is in mesh with the toothed rack portion 128 so as to move the upper section 126b to the left or right in FIG. 9B. A distance scale 180 is provided on the platform 144 to measure the movement of the upper section 126b relative to lower section 126a.

The cervical measuring pad 122 includes a resilient core 122a of foamed plastic for example and an outer plastic sheet or shell 122b, both of which are resilient so as to be capable of being reshaped in a manner to be described below.

Figure 9B:
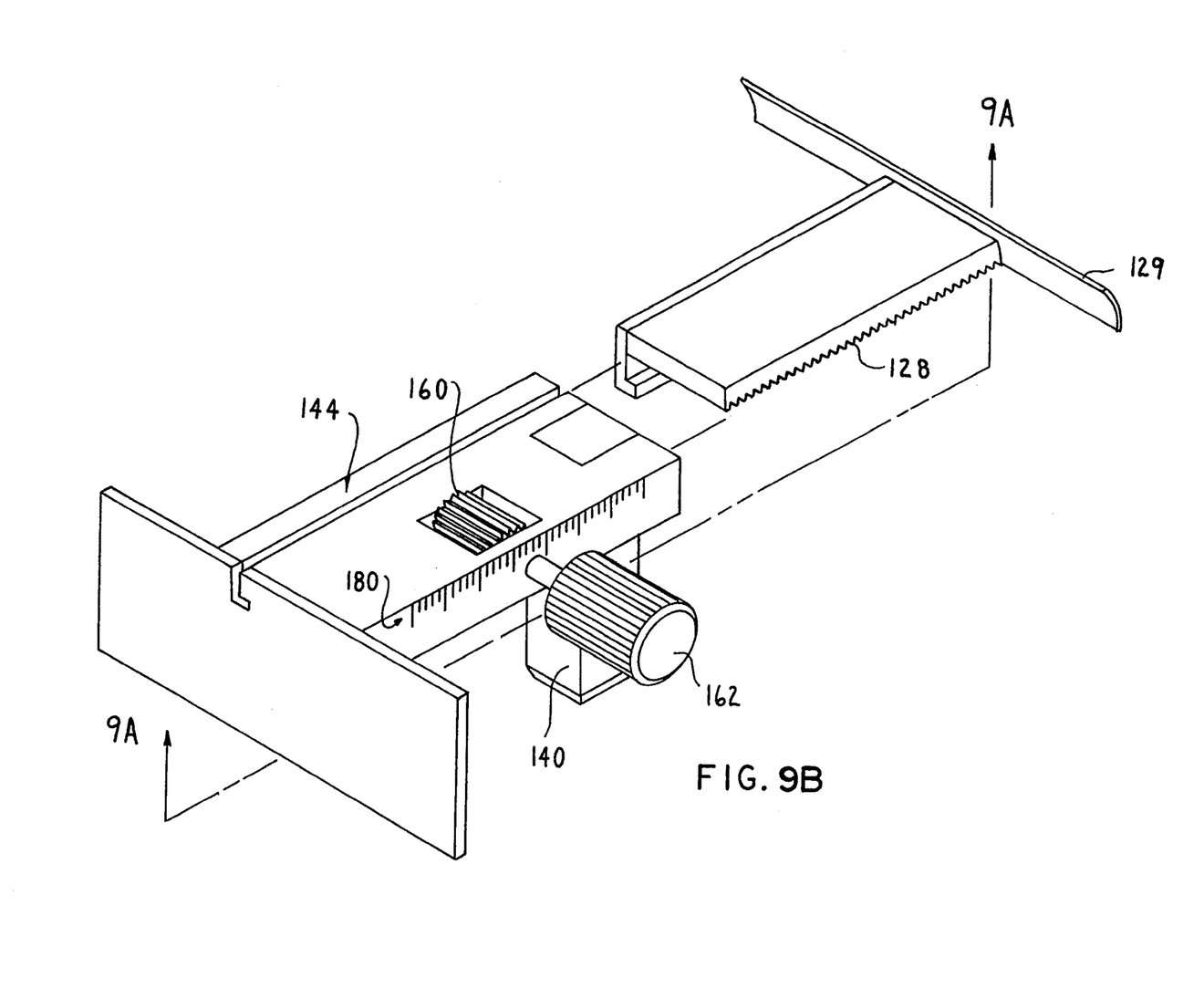
FIG. 9B is a perspective view of the pad section movement mechanism of the pad assembly of FIG. 9A.

The upper section 126b includes an arcuate member 129 that engages the outer plastic sheet or shell 122b of the measuring pad 122 such that lateral movement of the upper section 126b to the right in FIGS. 9A, 9B will cause the measuring pad to be stretched and flattened somewhat to reduce the curvature of the outer shell and movement to the left in FIGS. 9A, 9B will cause the measuring pad to be contracted and rounded somewhat to increase the curvature of the outer shell. As a result, the configuration/size of the cervical measuring pad 122 can be adjusted in-situ while it is positioned on the base enclosure 43 of the measuring means 20 to accommodate the patient's neck curvature/size. The curvature and adjusted length of the measuring pad 122 can be determined and recorded for use as parameters in the fabrication of a cervical pillow custom fit to the patient.

Use of the cervical measuring pad 122 may eliminate the need to maintain an inventory of measuring pads of the type shown in FIGS. 7A through 7G, or at least can reduce the number of measuring pads in inventory.

Figure 10:
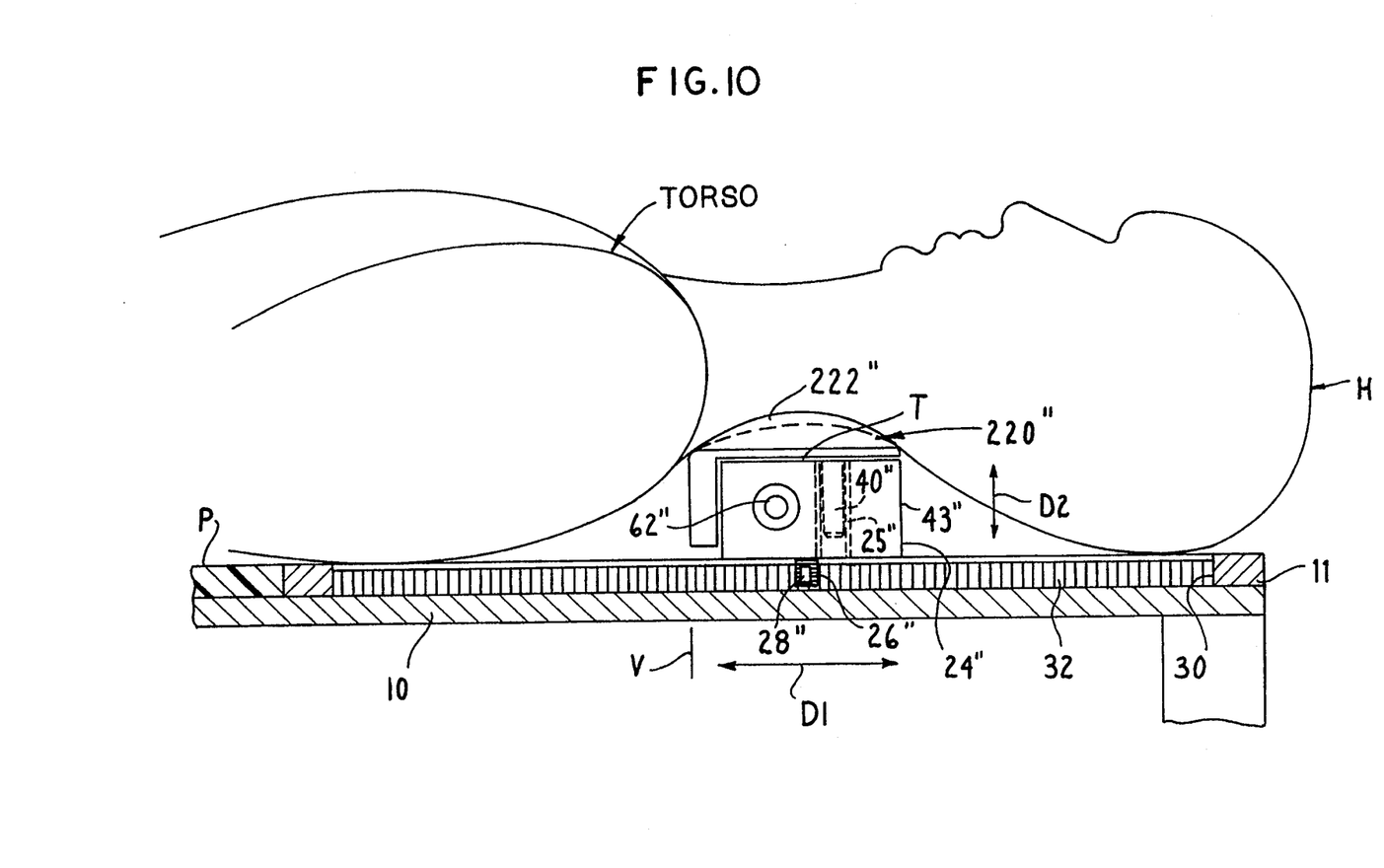
FIG. 10 is a sectioned side elevation of a traction pad measuring apparatus in accordance with another embodiment of the invention.

Referring to FIG. 10, a measuring apparatus in accordance with another embodiment of the invention is illustrated for determining parameters of a patient's neck that will allow the fabrication of a cervical traction pillow to configurations and sizes in accordance with the measured parameters so to enable the manufacture of a cervical traction pillow custom-fit to that patient.

The measurement apparatus can comprise the aforementioned table 10 having the horizontal upper surface 12 and a pad P for properly positioning the patient's torso during measurement; e.g. the back of the patient's torso as shown best in FIG. 10. The apparatus also includes the base member 11 described above. The base member 11 is used to properly position the back of the patient's head H as shown in FIG. 10. The base member 11 typically is set onto the table 10 in the manner described above with respect to FIGS. 1–2.

The parameters used in the fabrication of the traction pillow are obtained from the patient by the measuring means 200" disposed on the base member 11. To this end, the measuring means 220" is constructed in the same manner as measuring means 20 (with exception of traction pad 222") wherein like features bear like reference numerals double primed that permits a particular traction measuring pad 222" to be moved in a first direction D1 corresponding to the length of the patient's neck between the torso and the head H and in a second direction D2 transverse to the first direction toward the concavity of the patient's neck (i.e. in a vertical direction in FIGS. 10).

To this end, the measuring means 220" includes the aforementioned base 24" mounted on the base member 11 for movement relative thereto in the first direction D1 and traction measuring pad 222" mounted on the base 24" for movement relative thereto in the second direction D2. The base enclosure 43" includes the threaded shaft 26" extending downwardly from the bottom thereof into the groove 30 formed in the base member 11, all as described above with respect to FIGS. 1–2. The shaft 26" includes a laterally extending, ratchet-engaging cross member 28" like ratchet-engaging member 28 of FIGS. 2–3 to engage the ratchet teeth 32 formed on an undercut shoulder formed in the groove 30 in the base member 11 as shown in FIG. 10 and also in FIGS. 2-3 for the first embodiment of the invention. 1-2. The base enclosure 43" is manually moved in the direction D1 to provide ratchet-type movement of the cross member 28" relative to the ratchet teeth 32 in order to adjust the position of the measuring means 220" in the direction D1.

A particular traction measuring pad 222" (selected from an inventory of differently profiled pads in the manner described above) is disposed on a tubular support post 40" that is received in a tubular member (not shown but like tubular member 25 of FIG. 2) for vertical movement relative thereto in the vertical direction D2. The measuring pad 222" includes a lower metal, plastic or wood platform or base member 244", FIG. 11A, to which the post 40" is connected. The pad 222" is mounted on the platform 244" and includes a grooved, flat front elevational upper surface profile 243", FIG. 11B, and an arcuate side elevational upper surface profile 245", FIG. 11A, at least a portion of which is defined by radius R that, as will be explained, is selected by the operator of the apparatus in dependence on the curvature of the patient's neck; i.e. to match the curvature of the patient's neck. The pad 222" includes a longitudinally extending groove 247" molded therein to accommodate the patient's spinal vertebrae.

Figure 11A:
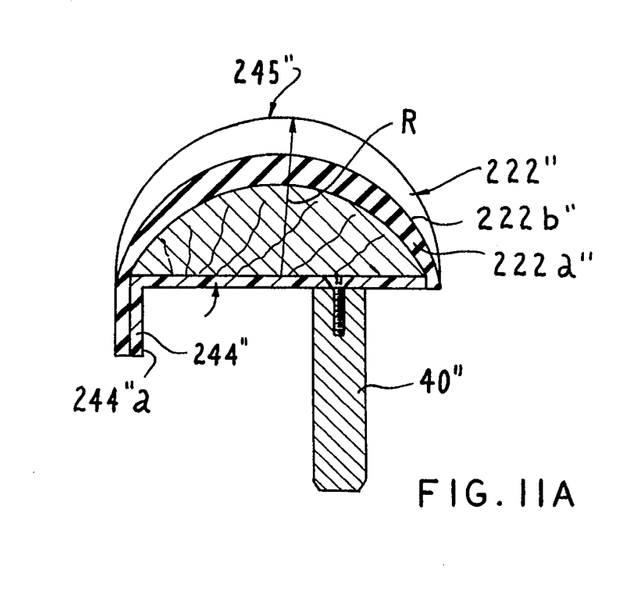
FIGS. 11A, 11B, and 11C are respective sectional, front, and plan elevational views of the traction pad assembly of FIG. 10.
Figure 11B:
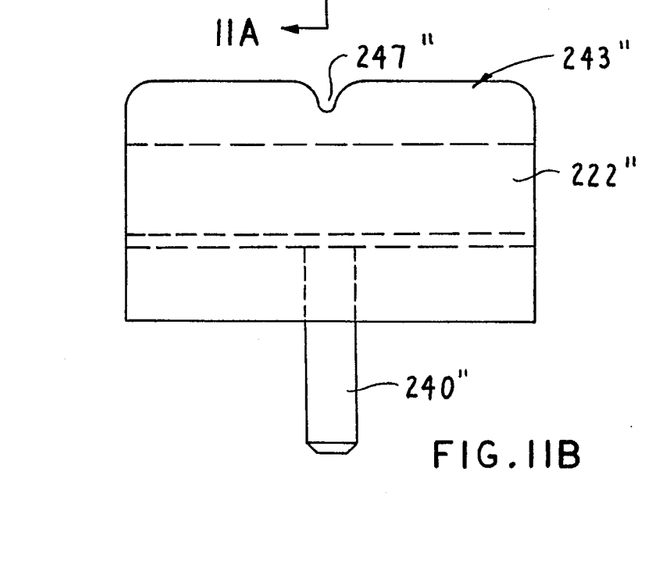
Figure 11C:
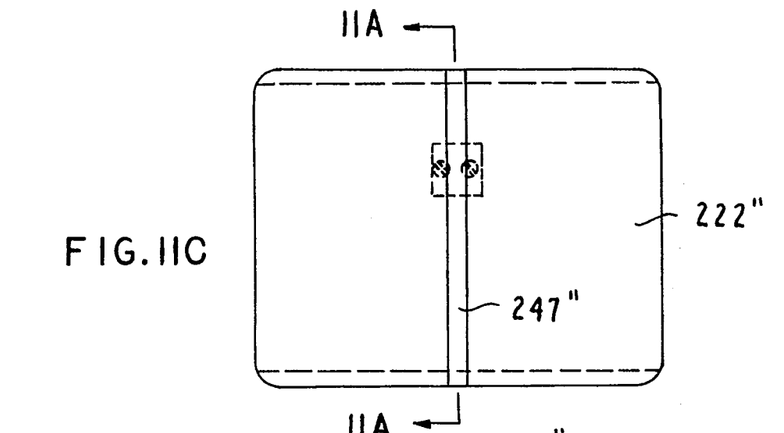

The pad 222" may comprise a molded plastic foam core 222a" covered by a plastic outer sheet or shell 222b" as shown, for example, in FIG. 11A. Other types of pad constructions can be used, however, in the invention.

The lower platform 244" includes a depending flange 244a" overlapping the base enclosure 43" on the side thereof facing the patient's torso. The flange 244a" provides a vertical reference V relative to which the patient's shoulder in FIG. 10 is positioned prior to measurement taking.

A manually actuated pad moving means (not shown but like moving means 50 described above with respect to FIG. 1-3) is provided for moving the traction measuring pad 222" in the second direction D2 to engage the cervical region of the patient when the patient's torso and head are positioned for measurement as shown in FIG. 10. The pad moving means is actuated by a manually rotatable knob 62" in the same manner as described above for moving means 50.

To conduct the traction pad measurement, the patient is properly positioned on the table 10 and base member 11 as shown in FIG. 10. The base enclosure 43" of the measuring means 220" is initially located at the particular reference position indicator R1, R2, R3 or the like (not shown but see FIG. 1) in dependence on the particular measuring pad 222" chosen by the operator.

The base enclosure 43" then is moved manually (providing ratchet action between cross member 28" and teeth 32) from the particular reference position in the longitudinal direction D1 to provide a best fit to the length of the patient's neck. This movement corresponds to a distance that is determined from a linear distance scale (not shown but similar to scale 80) disposed proximate the groove 30. This distance comprises one parameter to be used in fabrication of the traction pillow or pad for the patient. As a result, the longitudinal distance of base movement is recorded by the operator of the apparatus.

Then, the measuring pad 222" is raised by rotation of knob 62" until the pad 222" is snugly fit to the back of the patient's neck curvature. The distance that the pad 222" is raised is determined from a linear distance scale (like scale 82) on the post 40" using the top surface T" of the base enclosure 43" as the reference line for sighting. The distance is recorded and is another parameter used to fabricate the traction pillow or pad for the patient.

The distances that the base 24" and the measuring pad 222" are moved in the respective first and second directions D1, D2 to engage the cervical pad with the cervical region of the patient as well as the selected profile of the measuring pad 222" selected for the measurement (i.e. radius R) provide parameters that are recorded and used in the manufacture of a traction pad custom-fit to the patient.

In lieu of the measuring pad 222" shown in FIGS. 10, the measuring pad 222" shown in FIGS. 9A, 9B and described in detail above can be used in determining the parameters for fabricating the traction pillow or pad. As mentioned, the configuration/size of the measuring pad 222" can be adjusted in-situ while it is positioned on the base enclosure 24" of the measuring means 220" to accommodate the patient's neck curvature/size. The curvature of the measuring pad can be determined and recorded for use as parameters in the fabrication of a traction pillow or pad custom fit to the patient.

While the invention has been described with respect to certain specific embodiments thereof, it will understood by those skilled in the art that various modifications and substitutions can be made thereto without departing from the spirit and scope of the invention as set forth in the following claims.

The embodiments of the invention in which an exclusive property or privilege is claimed are defined as follows:

What is claimed is:

1. Measurement apparatus for determining parameters of a patient's neck, comprising:
   horizontal support means for positioning the patient's torso and head during measurement to direct the weight of the torso and the head downwardly toward said horizontal support means, and
   measuring means for moving cervical measuring means in a first horizontal direction corresponding to the length of the patient's neck between the torso and the head and in a second vertical direction transverse to the first direction toward the concavity of the patient's neck, said measuring means including base means movable in said first direction, said cervical measuring means being movably mounted on said base means for movement relative thereto in said second direction and having an arcuate profile selected in dependence on the curvature of the patient's neck, and means for moving said cervical measuring means in said second direction to engage the cervical region of the patient when the patient's torso and head are positioned for measurement, the distances that said base means and said cervical measuring means are moved in the respective first and second directions to engage said cervical measuring means with the cervical region of the patient and the selected profile of said cervical measuring means providing parameters for the manufacture of a cervical pillow for use by the patient.

2. The apparatus of claim 1 including a base member on which said measuring means is disposed.

3. The apparatus of claim 2 wherein said base member includes a plurality of reference position indicators spaced along said first direction proximate the base means of said measuring means, each indicator providing a respective reference measurement start position for said base means in dependence on the particular cervical measuring means profile selected.

4. The apparatus of claim 3 wherein said base member includes distance scale means proximate said indicators for determining the distance that said base means of said measuring means is moved relative to a respective reference position.

5. The apparatus of claim 4 wherein said measuring means includes distance scale means for determining the distance that said cervical pad moving means is moved to engage said cervical measuring means with the patient's neck.

6. The apparatus of claim 2 wherein said base member includes head positioning means disposed thereon in alignment with said measuring means in said first direction for movement in said first direction independent of movement of said measuring means so as to be positioned to support the patient's head during measurement.

7. The apparatus of claim 6 wherein said head positioning means comprises base means movably mounted on said base member for movement in said first direction, head pad means movably mounted on said base means for movement in a direction parallel to said second direction, means for moving said head pad means to engage and support the head of the patient during measurement.

8. The apparatus of claim 6 wherein said base means of said measuring means and said base means of said head positioning means each include a shaft means disposed in a common groove in said base member.

9. The apparatus of claim 8 wherein said base member includes ratchet teeth in said groove and said shaft means each includes a lateral teeth engaging member to position the respective measuring means and head positioning means relative to reference positions on said base member.

10. The apparatus of claim 1 wherein said cervical measuring means comprises relatively movable sections that permit variations in the curvature and length thereof.

11. The apparatus of claim 1 having weight measuring means operably associated with said measuring means and with said head positioning means.

12. Measurement apparatus for determining parameters of a patient's neck, comprising:
    table means for positioning the patient's torso during measurement,
    head positioning means for positioning the patient's head during measurement, and
    measuring means for moving a cervical measuring pad in a first direction corresponding to the length of the patient's neck between the torso and the head and in a second direction transverse to the first direction toward the concavity of the patient's neck, said measuring means including base means movably mounted on said table means for movement relative thereto in said first direction, said cervical measuring pad being movably mounted on said base means for movement relative thereto in said second direction and having an arcuate profile selected in dependence on the curvature of the patient's neck, and means for moving said cervical measuring pad in said second direction to engage the cervical region of the patient when the patient's torso and head are positioned for measurement, the distances that said base means and said cervical measuring pad means are moved in the respective first and second directions to engage said cervical measuring pad with the cervical region of the patient and the selected profile of said cervical measuring pad providing parameters for the manufacture of a cervical pillow for use by the patient.

13. The apparatus of claim 12 wherein said head positioning means comprises base means movable in said first direction, head pad means movably mounted on said base means for movement in a direction parallel to said second direction, means for moving said head pad means to engage and support the head of the patient during measurement.

14. Measuring apparatus for determining parameters of a patient's neck, comprising:
    means for positioning the back of the patient's torso and back of the head in a downwardly facing position during measurement, and
    measuring means for moving a cervical traction pad means in a first direction corresponding to the length of the patient's neck between the torso and the head and in a second direction transverse to the first direction toward the concavity of the patient's neck, said measuring means including base means movably mounted on said table means for movement relative thereto in said first direction, said cervical traction pad means being movably mounted on said base means for movement relative thereto in said second direction and having an arcuate profile selected in dependence on the curvature of the patient's neck, and means for moving said cervical traction pad means in said second direction to engage the cervical region of the patient when the patient's torso and head are positioned for measurement, the distance that said base means and said cervical traction pad means are moved in the respective first and second directions to engage said cervical pad means with the cervical region of the patient and the selected profile of said cervical pad means providing parameters for the manufacture of a cervical traction pillow for use by the patient.

15. The apparatus of claim 14 wherein said cervical traction pad means comprises relatively movable sections that permit variations in the curvature thereof so as to provide a further parameter that also can be used in the manufacture of a traction pad.

16. The apparatus of claim 14 wherein the cervical traction pad means includes a longitudinal groove to accommodate the patient's spinal vertebrae during measurement.

17. The apparatus of claim 14 wherein said measuring means includes distance scale means for determining the distance that said cervical traction pad moving means is moved to engage said cervical pad means with the patient's neck.

18. Measurement apparatus for determining parameters of a patient's neck, comprising:
    means for positioning the patient's torso during measurement,
    measuring means disposed on a base member for moving cervical measuring means in a first direction corresponding to the length of the patient's neck between the torso and the head and in a second direction transverse to the first direction toward the concavity of the patient's neck, said measuring means including base means movable in said first direction, said cervical measuring means being movably mounted on said base means for movement relative thereto in said second direction and having an arcuate profile selected in dependence on the curvature of the patient's neck, means for moving said cervical measuring means in said second direction to engage the cervical region of the patient when the patient's torso and head are positioned for measurement, the distances that said base means and said cervical measuring means are moved in the respective first and second directions to engage said cervical measuring means with the cervical region of the patient and the selected profile of said cervical measuring means providing parameters for the manufacture of a cervical pillow for use by the patient, and head positioning means disposed on said base member in alignment with said measuring means in said first direction for movement in said first direction independent of movement of said measuring means so as to be positioned to support the patient's bead during measurement.

19. The apparatus of claim 18 wherein said head positioning means comprises base means movably mounted on said base member for movement in said first direction, head pad means movably mounted on said base means for movement in a direction parallel to said second direction, means for moving said head pad means to engage and support the head of the patient during measurement.

20. The apparatus of claim 18 wherein said base means of said measuring means and said base means of said head positioning means each include a shaft means disposed in a common groove in said base member.

21. The apparatus of claim 20 wherein said base member includes ratchet teeth in said groove and said shaft means each includes a lateral teeth engaging member to position the respective measuring means and head positioning means relative to reference positions on said member.

22. Measurement apparatus for determining parameters of a patient's neck, comprising:

means for positioning the patient's torso and head during measurement, and measuring means for moving cervical measuring means in a first direction corresponding to the length of the patient's neck between the torso and the head and in a second direction transverse to the first direction toward the concavity of the patient's neck, said measuring means including base means movable in said first direction, said cervical measuring means being movably mounted on said base means for movement relative thereto in said second direction and comprising relatively movable sections that permit variations in the curvature and length of said cervical measuring means in dependence on the curvature of the patient's neck, and means for moving said cervical measuring means in said second direction to engage the cervical region of the patient when the patient's torso and head are positioned for measurement, the distances that said base means and said cervical measuring means are moved in the respective first and second directions to engage said cervical measuring means with the cervical region of the patient and the selected profile of said cervical measuring means providing parameters for the manufacture of a cervical pillow for use by the patient.

* * * * *